US011696993B2

(12) United States Patent
Mansfield et al.

(10) Patent No.: US 11,696,993 B2
(45) Date of Patent: **\*Jul. 11, 2023**

(54) SYSTEM AND METHOD FOR USE OF ACOUSTIC REFLECTOMETRY INFORMATION IN VENTILATION DEVICES

(71) Applicant: Covidien LP, Mansfield, MA (US)

(72) Inventors: Jeffrey P. Mansfield, Carmel, IN (US); Catherine Johnson-Tieck, Carmel, IN (US)

(73) Assignee: Covidien LP, Mansfield, MA (US)

( * ) Notice: Subject to any disclaimer, the term of this patent is extended or adjusted under 35 U.S.C. 154(b) by 376 days.

This patent is subject to a terminal disclaimer.

(21) Appl. No.: 16/947,796

(22) Filed: Aug. 17, 2020

(65) Prior Publication Data

US 2020/0376218 A1 Dec. 3, 2020

Related U.S. Application Data

(60) Continuation of application No. 15/623,666, filed on Jun. 15, 2017, now Pat. No. 10,751,492, which is a
(Continued)

(51) Int. Cl.
*A61M 16/04* (2006.01)
*A61M 16/00* (2006.01)
*A61M 16/08* (2006.01)

(52) U.S. Cl.
CPC ........ *A61M 16/04* (2013.01); *A61M 16/0051* (2013.01); *A61M 16/024* (2017.08);
(Continued)

(58) Field of Classification Search
CPC .............. A61M 16/00; A61M 16/0051; A61M 16/024; A61M 16/04; A61M 16/0411;
(Continued)

(56) References Cited

U.S. PATENT DOCUMENTS 2,209,944 A  7/1940 Walker
4,344,436 A  8/1982 Kubota
(Continued)

FOREIGN PATENT DOCUMENTS

EP   1166813      1/2002
WO   2009149351   12/2009
(Continued)

OTHER PUBLICATIONS

U.S. Appl. No. 17/198,818, filed Mar. 11, 2021, Gardner J. Kimm.
(Continued)

*Primary Examiner* — Joseph D. Boecker

(57) ABSTRACT

The present disclosure relates to a system and method for use of acoustic reflectometry information in ventilation devices. The system and method includes a speaker to emit sound waves into an intubated endotracheal tube ("ETT") and a microphone to detect returning acoustic reflections. In addition, the system and method includes a reflectometry device in communication with a ventilation device for analyzing timings and amplitudes of the returning acoustic reflections to determine a size of a passageway around an ETT tip, location and size of ETT obstructions, and relative movement of the ETT tip within a trachea. The reflectometry device is also configured to determine a resistance parameter representative of resistance to actual flow of air through the ETT based upon a function of the diameter of the ETT, length of the ETT, and percent obstruction of the ETT, where the resistance parameter is used to calculate the tracheal pressure.

20 Claims, 3 Drawing Sheets

Related U.S. Application Data division of application No. 13/853,252, filed on Mar. 29, 2013, now Pat. No. 9,707,363.

(60) Provisional application No. 61/617,249, filed on Mar. 29, 2012.

(52) U.S. Cl.
CPC ..... *A61M 16/0833* (2014.02); *A61M 16/0411* (2014.02); *A61M 2016/0027* (2013.01); *A61M 2205/3375* (2013.01); *A61M 2205/502* (2013.01); *A61M 2205/581* (2013.01); *A61M 2230/46* (2013.01)

(58) Field of Classification Search
CPC .. A61M 2205/3375; A61M 2016/0027; A61M 2230/46
See application file for complete search history.

(56) References Cited

U.S. PATENT DOCUMENTS

| | | | |
|---|---|---|---|
| 4,501,273 A | 2/1985 | McGinnis | |
| 4,630,606 A | 12/1986 | Weerda | |
| 4,697,593 A | 10/1987 | Evans | |
| 4,700,396 A | 10/1987 | Bolin | |
| 5,445,144 A * | 8/1995 | Wodicka | A61M 16/202 |
| | | | 128/207.14 |
| 5,575,310 A | 11/1996 | Kamen | |
| 5,655,518 A | 8/1997 | Burden | |
| 5,666,960 A | 9/1997 | Fredberg | |
| 5,823,965 A | 10/1998 | Rasmussen | |
| 5,853,005 A | 12/1998 | Scanlon | |
| 6,257,234 B1 | 7/2001 | Sun | |
| 6,390,091 B1 | 5/2002 | Banner | |
| 6,443,907 B1 | 9/2002 | Mansy | |
| 6,629,527 B1 | 10/2003 | Estes | |
| 6,705,319 B1 * | 3/2004 | Wodicka | A61M 16/0488 |
| | | | 128/207.14 |
| 6,761,693 B1 | 7/2004 | Rasmussen | |
| 7,347,824 B2 | 3/2008 | Wilkinson | |
| 7,691,070 B2 | 4/2010 | Comanducci | |
| 7,708,697 B2 | 5/2010 | Wilkinson | |
| 7,850,618 B2 | 12/2010 | Wilkinson | |
| 7,891,354 B2 | 2/2011 | Farbarik | |
| 8,038,629 B2 | 10/2011 | Solanki | |
| 8,152,751 B2 | 4/2012 | Roger | |
| 8,280,489 B2 | 10/2012 | Li | |
| 8,371,303 B2 | 2/2013 | Schaner | |
| 8,394,031 B2 | 3/2013 | Mansy | |
| 8,424,529 B2 | 4/2013 | Efrati | |
| 8,522,787 B2 | 9/2013 | Lin | |
| 8,608,658 B2 | 12/2013 | Burbank | |
| 8,611,984 B2 | 12/2013 | Greenburg | |
| 8,764,725 B2 | 7/2014 | Averbuch | |
| 8,844,534 B2 | 9/2014 | Behlmaier | |
| 8,905,029 B2 | 12/2014 | Colburn | |
| 9,364,180 B2 | 6/2016 | Armitstead | |
| 9,498,590 B2 | 11/2016 | Mansfield | |
| 9,707,363 B2 * | 7/2017 | Mansfield | A61M 16/0051 |
| 10,668,240 B2 | 6/2020 | Mansfield | |
| 10,729,621 B2 | 8/2020 | Mansfield | |
| 10,751,492 B2 * | 8/2020 | Mansfield | A61M 16/0833 |
| 10,780,238 B2 | 9/2020 | Efrati | |
| 2001/0004893 A1 | 6/2001 | Biondi | |
| 2002/0016610 A1 | 2/2002 | Hovanes | |
| 2002/0053345 A1 * | 5/2002 | Jafari | A61M 16/205 |
| | | | 128/204.23 |
| 2002/0104537 A1 | 8/2002 | Banner | |
| 2003/0034035 A1 * | 2/2003 | Raphael | A61M 16/0411 |
| | | | 128/207.14 |
| 2005/0005935 A1 | 1/2005 | Gradon | |
| 2006/0070623 A1 | 4/2006 | Wilkinson | |
| 2006/0070624 A1 | 4/2006 | Kane | |
| 2006/0081255 A1 | 4/2006 | Miller | |
| 2006/0107962 A1 | 5/2006 | Ward | |
| 2007/0137652 A1 | 6/2007 | Qureshi | |
| 2007/0257788 A1 | 11/2007 | Carlson | |
| 2008/0078248 A1 | 4/2008 | Farbarik | |
| 2008/0078390 A1 | 4/2008 | Milne | |
| 2009/0025728 A1 | 1/2009 | Aljuri | |
| 2009/0082676 A1 | 3/2009 | Bennison | |
| 2009/0099479 A1 | 4/2009 | Solanki | |
| 2009/0120439 A1 | 5/2009 | Goebel | |
| 2009/0187164 A1 | 7/2009 | Rowe | |
| 2009/0229605 A1 | 9/2009 | Efrati | |
| 2009/0229611 A1 | 9/2009 | Martin | |
| 2009/0301601 A1 | 12/2009 | Enerson | |
| 2009/0318805 A1 | 12/2009 | Raphael | |
| 2010/0252048 A1 | 10/2010 | Young | |
| 2010/0261996 A1 | 10/2010 | Li | |
| 2011/0030694 A1 | 2/2011 | Schaner | |
| 2011/0087123 A9 | 4/2011 | Choncholas | |
| 2011/0154241 A1 | 6/2011 | Skidmore | |
| 2011/0197885 A1 | 8/2011 | Wondka | |
| 2011/0197888 A1 | 8/2011 | Deutsch | |
| 2011/0313689 A1 * | 12/2011 | Holley | A61B 5/097 |
| | | | 702/56 |
| 2012/0132211 A1 | 5/2012 | Halperin | |
| 2012/0232411 A1 | 9/2012 | Brunner | |
| 2013/0098363 A1 | 9/2013 | Forte | |
| 2013/0228171 A1 | 9/2013 | Mansfield | |
| 2013/0255691 A1 | 10/2013 | Mansfield | |
| 2013/0281885 A1 | 10/2013 | Rowbottom | |
| 2014/0051989 A1 | 2/2014 | McGowan | |
| 2014/0058253 A1 | 2/2014 | Prough | |
| 2014/0155720 A1 | 6/2014 | Stanislaus | |
| 2014/0249428 A1 | 9/2014 | Ingold | |
| 2014/0366874 A1 * | 12/2014 | Deutsch | A61B 5/7278 |
| | | | 128/202.13 |
| 2016/0279366 A1 | 9/2016 | Mansfield | |
| 2017/0043110 A1 | 2/2017 | Mansfield | |
| 2017/0340522 A1 | 11/2017 | Mansfield | |
| 2019/0038862 A1 | 2/2019 | Mansfield | |

FOREIGN PATENT DOCUMENTS

| | | |
|---|---|---|
| WO | 2010141415 | 12/2010 |
| WO | 2013134166 | 9/2013 |
| WO | 2013149138 | 10/2013 |
| WO | 2016154607 | 9/2016 |

OTHER PUBLICATIONS

J. Ferdinand Fiastro, Michael P. Habib, Stuart F. Quan; "Pressure Support Compensation for Inspiratory Work due to Endotracheal Tubes and Demand Continuous Positive Airway Pressure"; Chest, 93(3), Mar. 1988, 499-505.

F. Lofaso, B. Louis, L. Brochard, A. Haaf, and D. Isabey; "Use of the Blasius Resistance Formula to Estimate the Effective Diameter of Endotrachael Tubes"; American Review of Respiratory Disease, vol. 146, No. 4 (1992), pp. 974-979. doi: 10.1164/ajrccm/146.4.974.

Boqué, M.C., Gualis, B., Sandiumenge, A. et al. Endotracheal tube intraluminal diameter narrowing after mechanical ventilation: use of acoustic reflectometry. Intensive Care Med 30, 2204-2209 (2004). https://doi.org/10.1007/s00134-004-2465-1.

Stefan Schumann, Michael Lichtwarck-Aschoff, Christoph Haberth, Claudius A. Stahl, Knut Moller, Josef Gullmann: "Detection of partial endotracheal tube obstruction by forced pressure oscillations"; Respiratory Physiology & Neurobiology 155 (2007) 227-233.

"International Preliminary Report on Patentability written opinion dated Jul. 11, 2013 for PCT Application No. US 2013034599".

"Extended European search report and opinion dated Nov. 17, 2015 for EP Application No. 13770312.0".

\* cited by examiner

SYSTEM AND METHOD FOR USE OF ACOUSTIC REFLECTOMETRY INFORMATION IN VENTILATION DEVICES

I. CROSS REFERENCE TO RELATED APPLICATIONS

This application is a continuation of U.S. application Ser. No. 15/623,666, filed Jun. 15, 2017, which will issue on Aug. 25, 2020, as U.S. Pat. No. 10,751,492, which is a division of U.S. application Ser. No. 13/853,252, filed Mar. 29, 2013, now U.S. Pat. No. 9,707,363, issued Jul. 18, 2017, which claims the benefit of U.S. Provisional Application No. 61/617,249 filed Mar. 29, 2012, the disclosures of which are incorporated herein by reference in their entireties.

II. FIELD

The present disclosure is generally related to a system and method for use of acoustic reflectometry information in ventilation devices.

III. DESCRIPTION OF RELATED ART

When a hospital patient is unable to breathe on his own, the patient is connected to a mechanical ventilation device. The patient is first intubated, a procedure in which an endotracheal tube (also called an artificial airway, endotracheal tube, or ETT), is inserted through the nose or mouth into the trachea (wind pipe). The tube is then connected to a mechanical ventilation device, which forces air into the lungs.

Each year, approximately 60 million intubations requiring endotracheal tubes are performed worldwide. Assuring proper placement of the endotracheal tube within the trachea and assuring that it has not moved or become obstructed are significant clinical problems. Failure to correct a misplaced or clogged endotracheal tube can lead to serious complications to the patient, most notably conditions consistent with lack of oxygen such as brain damage or death.

Complications with endotracheal tubes include:

Unplanned Extubation: The endotracheal tube unexpectedly comes out of the patient's trachea. Unplanned extubation has an incidence rate of 10% in adult ICU patients.

Endobronchial Intubation: The endotracheal tube is placed too far down into the trachea, past the first branching, and enters a main stem bronchus (the airway pipe which leads to one of the two lungs) or, after proper positioning, patient movement or other factors cause the tube to advance into a bronchus.

Endotracheal Tube Obstruction: Lung secretions or other substances block the tube, the tube kinks in the patient's throat, or the patient bites excessively on the tube.

Esophageal intubation: The endotracheal tube is accidentally inserted into the esophagus (food pipe) instead of the trachea.

There are known in the art devices that provide direct, precise, real-time monitoring of endotracheal tube (ETT) position and obstructions, Systems and methods for doing this are disclosed in U.S. Pat. Nos. 5,445,144 and 6,705,319 to Wodicka et al. One such commercially available system is the SonarMed® AirWave™ system (available front SonarMed, Inc., 5513 W. 74th Street, Indianapolis, Ind. 46268). Such prior art devices and methodologies are collectively referred to herein as an "acoustic reflectometry system." The acoustic reflectometry system couples in-line between the ETT and the ventilator hose.

The acoustic reflectometry system's sound waves monitor the artificial y, alerting clinicians in real time of situations that may lead to unplanned extubations, ETT obstructions, endobronchial intubation, or esophageal intubation. Using principles similar to sonar, the acoustic reflectometry system sends a sound signal into the ETT and records the returning echoes that arise from within the tube and patient airways. The timing and amplitude of these echoes are analyzed by the system to non-invasively measure:

Passageway Size Around ETT Tip: The system analyzes the echo that comes from the tube tip to estimate the size of the passageway relative to tube diameter. This information may help clinicians identify and correct esophageal intubation and endobronchial intubation.

Degree and Location of Obstructions Within the ETT: The system analyzes the timing and amplitude of echoes that come from within the tube to estimate the location and size of obstructions. This may help clinicians identify an obstruction that forms in the endotracheal tube so it can be removed before the patient is harmed. It may also help the clinician differentiate patient biting or tube kinking from lung secretion buildup by noting the reported location of the obstruction.

ETT Tip Movement: The system estimates relative movements of the tube by tracking the timing of an echo that comes from within the lungs. This information may help clinicians identify and correct situations that can lead to unplanned extubation or endobronchial intubation.

Clinicians may use this information to assist with placing the ETT properly and to receive early warnings about tube movement and obstruction development so they may take corrective action to prevent patient harm.

An acoustic reflectometry system consists of an adapter connected to the proximal end of an ETT and to a monitor. Embedded inside the adapter is a sound generator such as a miniature speaker, for example, and at least one receiver such as a microphone array, for example. With these components, the system employs acoustic reflectometry by emitting sound waves from the speaker into an intubated ETT, detecting the returning acoustic reflections, or echoes, with the microphones, and then examining the echo timings and amplitudes to infer characteristics of the ETT and airway. The system's algorithms analyze the echo signal and provide information about the size of the passageway around the ETT tip, location and size of ETT obstructions, and relative movement of the ETT tip within the trachea.

The microphone array allows the system to determine the direction from which echoes arrive. As a result, the system can selectively filter all echoes that arise from devices on the ventilator side of the adapter, such as closed circuit suction catheters, Y-connectors, $ETCO_2$ sensors, and filters, for example. This selective filtering allows the system to obtain an echo waveform from the Ell and airways that is free of ventilator circuit echoes.

The human airways are a network of bifurcating branches starting at the trachea and ending at the alveoli—the small sacs where the oxygen and carbon dioxide exchange takes place. An interesting property of the airways is that even though the cross sectional area of each individual segment decreases as the branching depth increases, the total cross sectional area (arrived at by adding up the cross sectional areas of all parallel segments) undergoes a rapid increase after several generations of airway branching. In other words, the airways behave acoustically like a horn with a bell at the end, and sound waves traveling down the airways will be reflected at the bell. The negative pressure wave from this bell-shaped region is used by the system as a reference to which changes in ETT tip position are tracked. The bell begins around the 6th branching generation (approximately 5 cm past the carina in adults).

There is no echo from the carina that can be tracked. Unfortunately, since the additive cross sectional area of the two main stem bronchi is approximately equal to the trachea's cross sectional area, there are no echoes of significance that arise from the carina.

While a majority of medical devices that use acoustics operate in the ultrasonic frequency range, the acoustic reflectometry system operates in an audible range below 8 kHz because of the frequencies at which tubes behave as waveguides. Since the sounds typically found in the ventilator circuit—such as respiratory sounds, secretion sounds, or cuff leak sounds—can potentially interfere with the echo signals used by the system, a series of advanced data collection algorithms are used to obtain a clean echo signal during ventilation.

When connected to a patient, the acoustic reflectometry system collects a majority of its measurements during the quiet period of ventilation between end expiration and inspiration. As a result, the acoustic reflectometry system monitor provides updates to the ETT status approximately every patient breath, depending on the level of noise present between breaths. For cases where excessive noise interferes with acoustical measurements such that the ETT status is not updating, the acoustic reflectometry system gives the clinician the option to listen directly to the adapter microphones via the monitor speaker. This assists the clinician in determining the interfering noise source so they can rectify it if possible. Examples of interfering noise sources may include: a leaky ETT cuff, secretions in the airway and/or ETT, a high respiratory rate, a nebulizer, or patient coughing.

A shortcoming of the prior art ventilation device described above is that the ventilation device does not have specific information pertaining to the condition and location of the ETT in the patient. Consequently, if the ventilation device had access to acoustic reflectometry information, the performance of the ventilation device could be improved.

However, in view of the prior art at the time the present invention was made, it was not obvious to those of ordinary skill in the pertinent art how the identified needs could be fulfilled.

IV. SUMMARY

A system and method for use of acoustic reflectometry information in ventilation devices is disclosed. The system and method of the present disclosure includes information about the artificial airway that can be used by other medical devices monitoring the patient or patient airways to enhance the device's performance and the patient's quality of care. These enhancements include improving ventilation modes that automatically compensate for ETTs by using obstruction information to estimate breath by breath ETT resistance, providing additional insights to the clinician regarding patient work of breathing which may lead to improved outcomes of weaning the patient from the ventilator, improving treatment efficacy by making alarms more specific and directing the clinician to the most likely source causing the alarm, trending ETT position and patency information in concert with ventilation trended variables to make it easier to determine correlations between artificial airway issues and the patient airway status, improving secretion management by using trend of estimated ETT resistance to determine if suctioning is recommended and comparing estimated ETT resistance pre- and post-suctioning to determine efficacy of suctioning; and reducing nuisance alarms by detecting patient events such as coughing and directing the ventilator to ignore the event instead of issuing a high pressure alarm.

In a particular illustrative embodiment, the system includes a sound generator to emit sound waves into the ETT and at least one receiver to detect returning acoustic reflections. The system also includes a reflectometry device having at least one processor and a memory that is accessible to the processor for analyzing timings and amplitudes of the returning acoustic reflections to determine a size of a passageway around an ETT tip, location and size of ETT obstructions, and relative movement of the ETT tip within a trachea. In addition, a ventilation device is in communication with the reflectometry device.

Additional objects, features, and advantages of the present disclosure will become apparent to those skilled in the art upon consideration of the following detailed description of a preferred embodiment exemplifying the best mode of carrying out the teachings of the present disclosure as presently perceived.

VI. DETAILED DESCRIPTION

Figure 1:
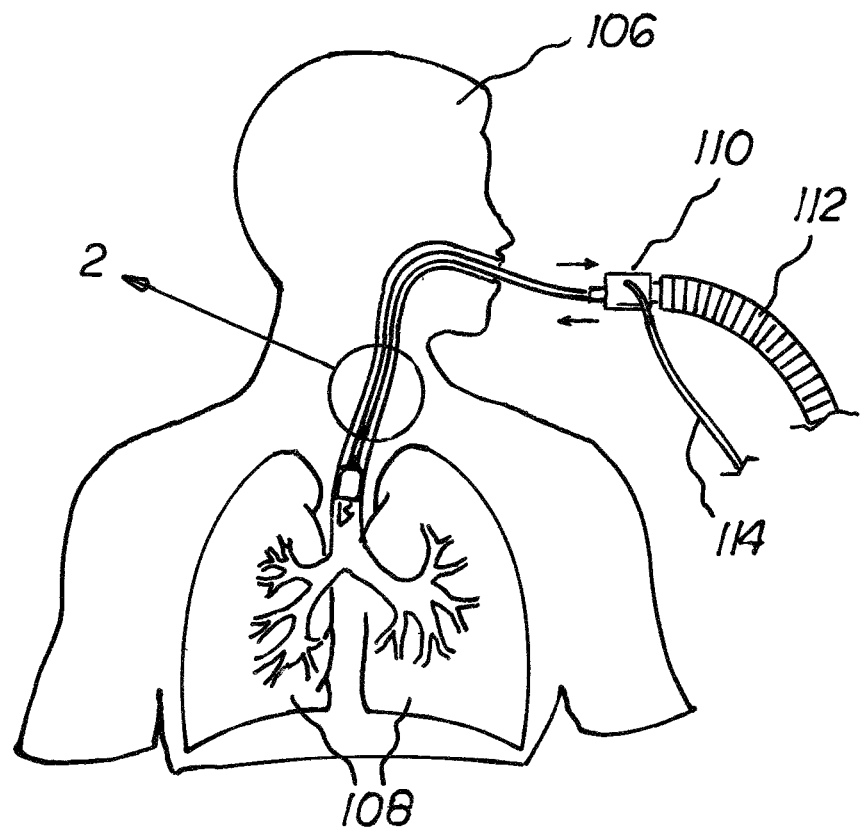
FIG. 1 is a diagrammatical view illustrating proper insertion of an endotracheal tube ("ETT") into a trachea of a human body.

For purposes of promoting an understanding of the principles of the method and system, reference will now be made to the embodiment illustrated in the drawings, and specific language will be used to describe that embodiment. It will nevertheless be understood that no limitation of the scope of the method and system is intended. Alterations and modifications, and further applications of the principles of the method and system as illustrated therein, as would normally occur to one skilled in the art to which the method and system relates are contemplated, are desired to be protected. Such alternative embodiments require certain adaptations to the embodiments discussed herein that would be obvious to those skilled in the art.

Figure 2:
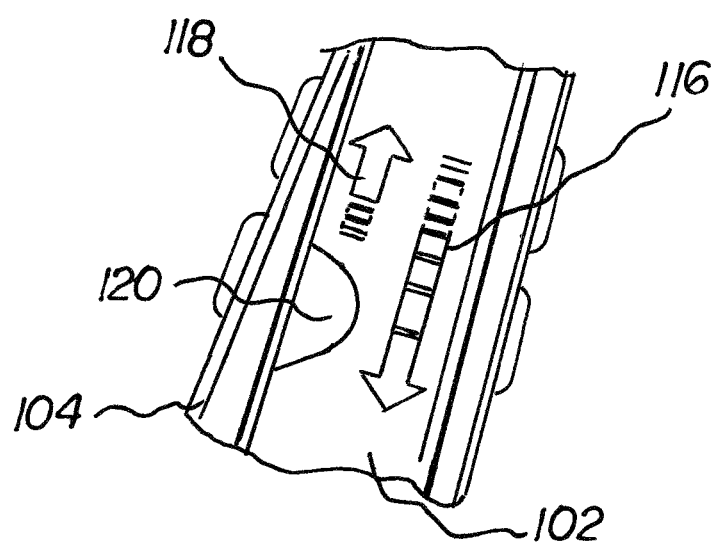
FIG. 2 is a diagrammatical view of sound waves and acoustic reflections moving within the ETT.

Referring now to the drawings, FIGS. 1 and 2 illustrate proper insertion of an ETT 102 into the trachea 104. For proper mechanical ventilation of the patient 106, it is important that distal end of the ETT 102 is positioned properly within trachea 104 between vocal folds and the carina to provide adequate ventilation to both lungs 108. The acoustic reflectometry system adapter 110 couples between the ETT 102 and the ventilator hose 112 as shown in FIG. 1. The acoustic reflectometry system's sound waves monitor the artificial airway, alerting clinicians in real time of situations that may lead to unplanned extubations, ETT obstructions, endobronchial or esophageal intubation. The adapter 110 is connected by a cord 114 (or wirelessly) to a device 122 to analyze signals from the system.

As shown in FIG. 2, the system uses principles similar to sonar as the acoustic reflectometry system sends a sound signal 116 into the FIT 102 and records the returning echoes 118 that arise from within the tube 102 and patient airways. The timing and amplitude of these echoes 118 are analyzed by the system to detect obstructions 120.

Figure 3:
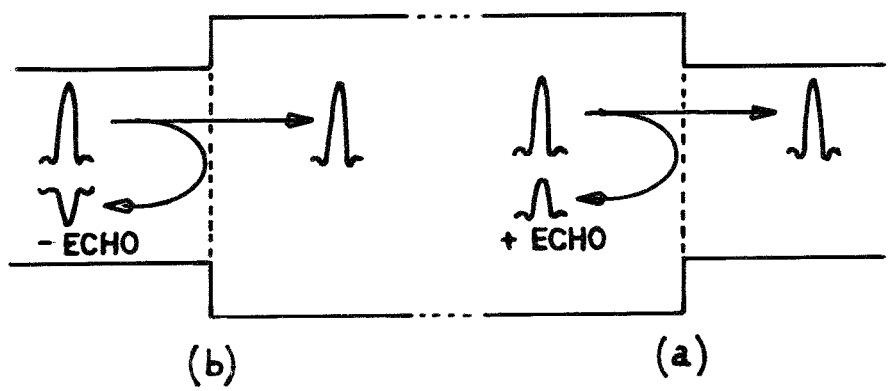
FIG. 3 is a diagrammatical view of the sound waves and respective echo signals (i.e., acoustic reflections) after encountering changes in cross sectional area in a tube.

Referring now to FIG. 3, as a sound wave travels inside a tube, a fraction of its energy reflects each time it meets with a change in cross sectional area. If it encounters a decrease in cross sectional area (see FIG. 3(a)), a positive pressure wave is reflected. This shows up as a positive deflection in the echo signal. If the sound wave encounters an increase in cross sectional area (see FIG. 3(b)), a negative pressure wave is reflected. This shows up as a negative deflection in the echo signal. The delay time of each echo identifies the distance from the microphone to the changing area that caused the echo. The amplitude of each echo identifies the approximate amount of area change.

Figure 4:
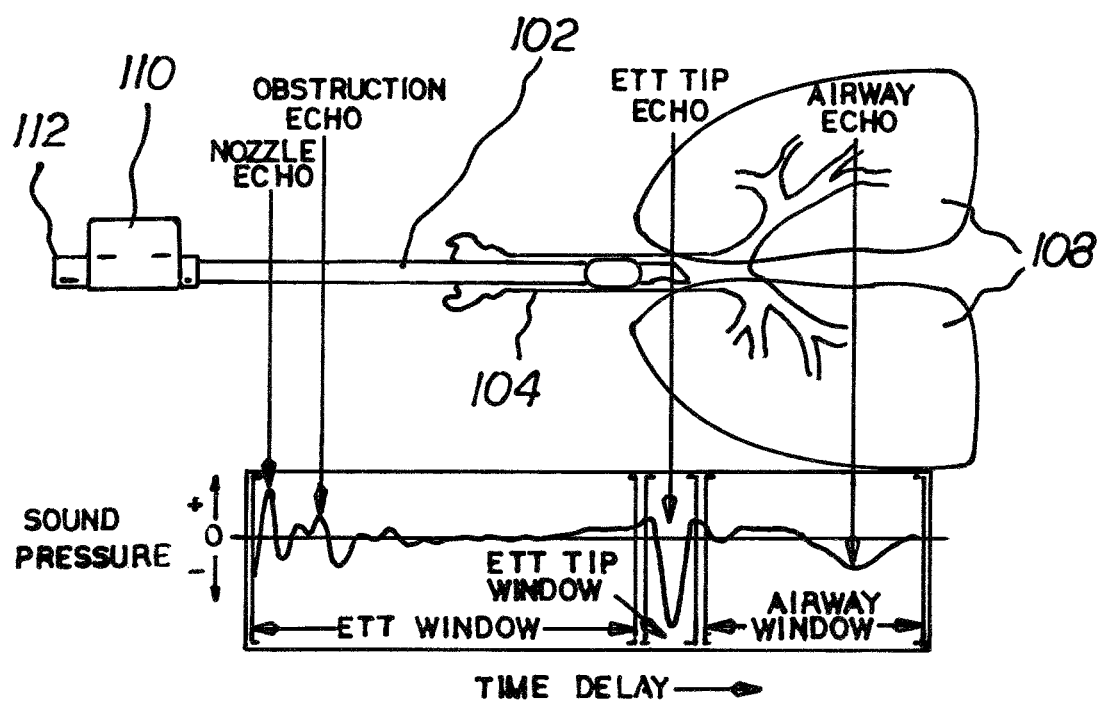
FIG. 4 is a diagrammatical view illustrating relationships between cross sectional area, amplitude, and time delay of an acoustic reflectometry system.

To illustrate the relationships between cross sectional area, amplitude, and time delay, FIG. 4 shows an intubated ETT (top) with its corresponding echo signal, as recorded by the acoustic reflectometry system (bottom). The pressure amplitude is represented on Y-axis and the time delay is represented on X-axis. For each deflection in the echo signal, an arrow denotes the corresponding region in the ETT and airways from which that echo arises.

The first echo is a positive deflection (positive pressure) indicating a cross sectional area decrease. This corresponds to the decrease in the nozzle's diameter from 9 mm to 8 mm. The second echo is a positive deflection immediately followed by a negative deflection, indicating a cross sectional area decrease and then an increase. This echo could be from a small obstruction in the ETT, from a kink in the ETT, or from a patient biting on the ETT. If the echo amplitude were larger, this would correspond to a larger obstruction. The acoustic reflectometry system estimates the obstruction size from the echo amplitude and the obstruction location from the echo delay time.

The third echo is a negative deflection indicating a cross sectional ea increase. This echo, referred to as the ETT tip echo, is analyzed by the acoustic reflectometry system to estimate the passageway size (or effective diameter) around the ETT. A negative deflection echo indicates that the ETT is located in a passageway that has a larger cross sectional area than the ETT. This would be the case for an EFT that is in the trachea. If this echo were to change to a positive deflection, it would indicate that the ETT is located in a passageway that has a smaller cross sectional area than the ETT. This may correspond to an ETT that is in the esophagus or bronchus or that it is clogged at the tip, for example, from mucus.

The last echo, referred to as the airway echo, arises from the bell shaped region in the lower airways. The acoustic reflectometry system tracks the time delay of this airway echo, estimating relative changes in the distance between the ETT tip and the airway echo region. For example, if the time delay between the ETT tip echo and the airway echo is decreasing (airway echo moving to the left), then this indicates that the ETT tip is getting closer to the airway echo region or that the ETT is migrating down the trachea.

Figure 5:
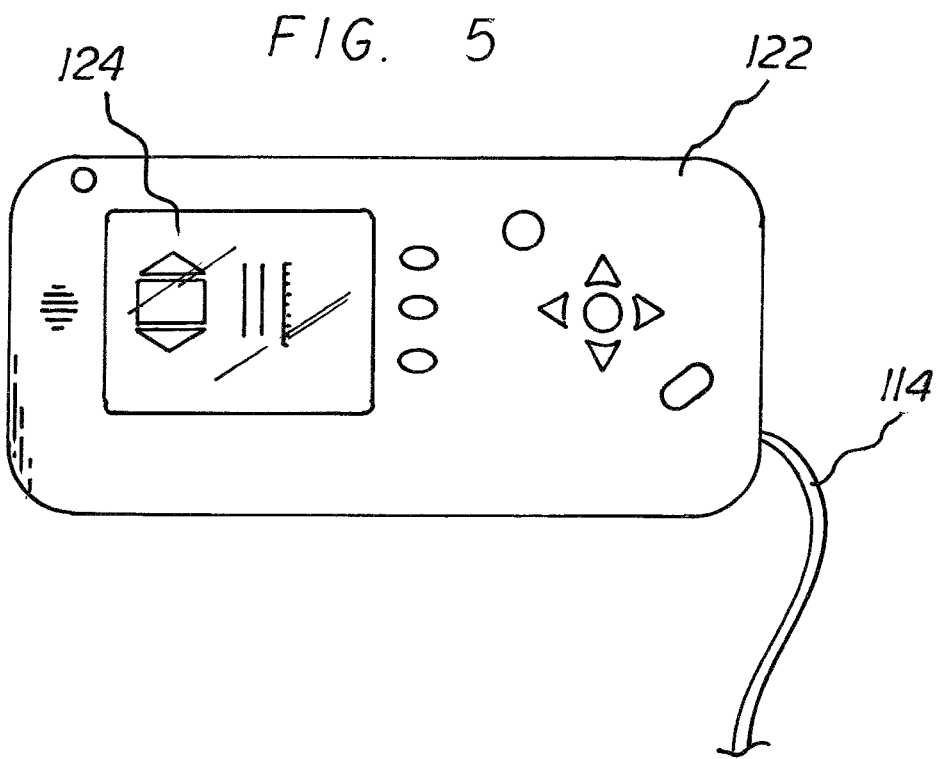
FIG. 5 is a diagrammatical view of a device of the system having a display, a processor and a memory that is accessible to the processor.
Figure 6:
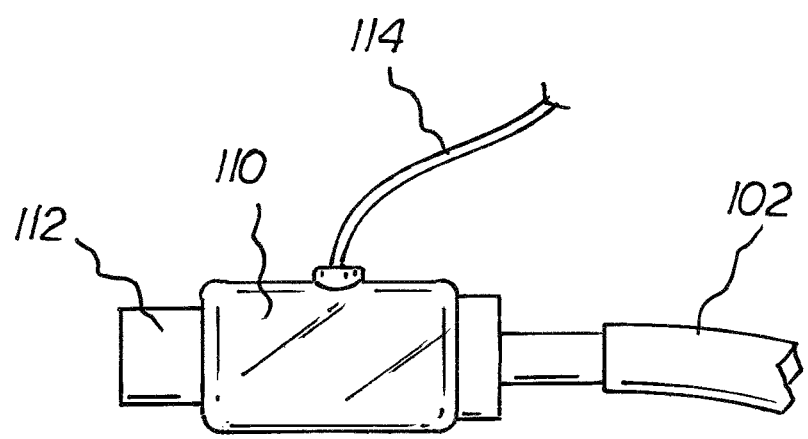
FIG. 6 is a diagrammatical view of an adapter of the system that inserts into the breathing circuit between the ventilator hose and the ETT.

Referring now to FIGS. 5 and 6, the acoustic reflectometry system includes a device 122 that is a handheld, portable device with a display 124 that provides information about the endotracheal tube position, obstruction, and movement. The device 122 has at least one processor and a memory that is accessible to the processor. The device 122 may include circuitry for sending, receiving and processing audio signals from the acoustic reflectometry system adapter 110 via cable 114. As explained below, the acoustic reflectometry system interprets the signals received from the patient's airway and provides feedback to the clinician through intuitive text and graphics.

Many improvements may be made in the operation of ventilators and other devices by obtaining information that may be gleaned from airway monitoring devices such as the acoustic reflectometry system disclosed herein and using this data and new algorithm to improve prior art ventilator functionality as described below.

Improvement in the Calculation of $P_{TRACHEA}$ (Pressure Within Trachea)

The pressure within the trachea can be calculated by a ventilator as follows:

$$P_{TRACHEA} = P_{AW} - \Delta P_{TUBE}$$

$$\Delta P_{TUBE} = R_{TUBE} \times \text{Flow}$$

where $P_{TRACHEA}$=estimated tracheal pressure,
$P_{AW}$=measured mean pressure at the Y-piece,
$\Delta P_{TUBE}$=estimated pressure drop across ETT,
$R_{TUBE}$=estimated ETT resistance (pressure differential across tube),
Flow=measured airway flow.

As explained above, in the prior art the calculation of $R_{TUBE}$ is a function of ETT diameter ($d_{ETT}$) and length (l). The prior art calculation of the estimated ETT resistance assumes an ideal tube for the ETT. However, in reality there are often obstructions within the ETT that can present a significant obstacle to the flow of air through the tube. The estimated ETT resistance may therefore be improved by using ETT monitoring data that can detect obstructions within the ETT, thereby allowing the calculation of $R_{TUBE}$ as a function $R_{TUBE}(d_{ETT}, l, Pct1, Pct2)$, which additionally takes into account percent of ETT obstruction 1 and 2. (Pct1 and Pct2, the two largest obstructions within the ETT). The figures for percent of ETT obstruction 1 and 2 (Pct1 and Pct2) comprise an estimate of what percent of the total ETT tube diameter is obstructed by each obstruction. Those skilled in the art will recognize that fewer or more than two tube obstructions may be taken into account. In fact, the acoustic reflectometry system can detect the whole obstruction profile within the ETT from the proximal end to the distal end and an effective tube diameter can be calculated based upon this data. The more accurate tube diameter measurement will allow for a more accurate estimate of the ETT tube resistance, and hence a more accurate estimate of $P_{TRACHEA}$.

Improvement to Automatic Tube Compensation

Work of breathing (WOB) is a measure of how much work an intubated patient has to do to inhale and exhale, and is used to determine if a patient will be able to breathe on their own if the ventilator is removed. An increase in $R_{TUBE}$ (tube resistance or the pressure across the tube) increases WOB. Automatic Tube Compensation (ATC) or Automatic Airway Compensation (AAC) is a technique used on the Draeger® Evita® (available from Draeger Medical, Inc., 3135 Quarry Road, Telford, Pa. 18969) Mallinckrodt® 840 (available from Covidien, 15 Hampshire Street, Mansfield, Mass. 02048), and Viasys® Avea® (available from CareFusion Corporation, 3750 Torrey View Court, San Diego, Calif. 92130) ventilators, which overcome the imposed work due to the ETT automatically, based on the known resistive characteristics of the ETT and the measured inspiratory flow. This technique is similar to the resistive component of proportional assist ventilation (PAV). ATC has been shown to reduce the imposed work of breathing due to the artificial airway more reliably than pressure support ventilation.

For ATC, the patient is spontaneously breathing and, depending on the flow volume, the ventilator calculates the pressure in the trachea and then assists the patient by setting the pressure at the proximal end of the ETT so that the calculated pressure in the trachea (i.e., after the pressure drop caused by the ETT) is at the pressure that would be present during normal breathing without an ETT Therefore, when the patient tries to spontaneously breathe, the ventilator senses a pressure drop and then increases the pressure at the proximal end of the ETT to compensate for the pressure drop. Setting "% tube compensation" on the ventilator to zero results in no compensation. Setting the "% tube compensation" to 100 provides full compensation for the ETT.

A typical operating sequence for initiating ATC is as follows:

1. The ventilator uses known constants for $R_{TUBE}$ for different size endotracheal and tracheostomy tubes stored in a look-up table.
2. The operator inputs the tube size and % tube compensation desired. The ventilator uses the mathematical model to simulate tracheal pressure control.
3. The ventilator also displays the calculated tracheal pressure.
4. The equation for tube compensation is $P_{TRACHEA} = P_{AW} - R_{TUBE} \times \text{Flow}$, where $P_{TRACHEA}$=tracheal pressure, $P_{AW}$=mean pressure at the Y-piece, $R_{TUBE}$=tube coefficient, Flow=airway flow.

This prior art technique suffers from the following pitfalls:

1. Airway secretion, or position changes may result in under compensation, since the calculated $P_{TRACHEA}$ has not taken these factors into account.
2. In vivo resistance is greater than ex vivo resistance.
3. Following extubation, upper airway changes may affect work of breathing unanticipated by tube compensation.

As described hereinabove, the obstruction information available from the acoustic reflectometry system may be used to improve the $P_{TRACHEA}$ estimate.

Improvements to Pressure Support Ventilation

Pressure support ventilation (PSV) is a ventilator mode that allows the user to select an elevated pressure during spontaneous inspiration to support breathing by overcoming the pressure drop across the ETT. This is somewhat similar to ATC, but instead the operator selects a constant pressure for support instead of the ventilator automatically calculating the pressure based on flow volume. Therefore, when selecting this mode, the user can use the real-time $P_{TRACHEA}$ calculated as described hereinabove as direct feedback to determine the appropriate pressure assist level. For example, while observing the real-time trachea pressure waveform, the user can adjust the pressure support level to obtain a trachea pressure that is above, at, or below a desired baseline pressure, depending on the amount of work the caregiver determines is appropriate as the patient progresses through the ETT weaning process.

Improvements to Adaptive Ventilation Modes

The process of gas delivery to the patient depends on the mode of ventilation (see below). Typically a breath can be classified as either volume controlled or pressure controlled, depending on which variable the ventilator actively controls during ventilation.

Volume ventilation—A predetermined tidal volume ($V_t$) is set by the clinician, and is delivered to the patient every time a breath is triggered. For example, if the tidal volume is set at 500 ml the ventilator will continue inspiration until 500 ml have been delivered to the patient. Upon completion of inspiration, the ventilator will cycle to exhalation. The amount of pressure necessary to deliver the tidal volume is determined by the resistance and compliance of the patient and ventilator circuit, and may vary from breath to breath.

Pressure ventilation—A predetermined peak inspiratory pressure (PIP) is set by the clinician and delivered to the patient throughout the set inspiratory time ($T_i$). After the inspiratory time has elapsed, the ventilator will cycle to expiration. The tidal volume delivered to the patient is determined by the resistance and compliance of the patient and circuit, and may vary from breath to breath.

Pressure regulated volume control—Several ventilator manufactures have incorporated features from both of these modes. These modes are now-variable, volume-targeted, pressure-regulated and time-limited. This means that instead of providing an exact tidal volume each breath, a target volume is set and the ventilator will vary the inspiratory pressure (PIP) on a breath to breath basis to achieve that volume. As with pressure ventilation, the inspiratory time ($T_i$) limits the length of the inspiratory cycle. The primary benefit from such modes is that they allow the set tidal volume to be achieved with the lowest possible peak inspiratory pressure.

Exhalation in mechanical ventilation is almost always completely passive. The ventilator's expiratory valve is opened, and expiratory flow is allowed until the baseline pressure (positive end-expiratory pressure, or PEEP) is reached. Expiratory flow is determined by patient factors such as compliance and resistance.

In Adaptive Support Ventilation (ASV), Inspiratory Pressure is the pressure above PEEP to be applied in the next breath. This pressure is measured at the proximal end of the ETT, Inspiratory pressure is adapted, breath by breath, to gently drive the tidal volume towards the $V_t$ target.

ASV delivers the optimal tidal volume using the lowest pressures possible using the following steps:

1. Assess breath by breath the patient's lung mechanics.
2. Optimize breath by breath the tidal volume/respiratory frequency combination based on lung mechanics.
3. Achieve optimum tidal volume/respiratory frequency by automatically adjusting mandatory rate and inspiratory pressure.

By using the much more accurate $R_{TUBE}$ resistance information that is made possible by the acoustic reflectometry system as discussed above, the much more accurate breath by breath estimation of ETT resistance can be used to help improve the estimate of patient lung mechanics (by better characterizing the contributions of the ETT to the overall mechanics). The $R_{TUBE}$ resistance information from the acoustic reflectometry system may therefore advantageously be made available to the ventilator controller that is assessing the patient's lung mechanics and adjusting the ventilator's mandatory rate and inspiratory pressure in order to improve optimization of tidal volume and respiratory frequency.

Use of $P_{TRACHEA}$ to Inform Selection of Ventilation Settings

As discussed above, pressure support ventilation (PSV) is a ventilator mode which allows the user to select an elevated pressure during spontaneous inspiration to support breathing by overcoming the pressure drop across the ETT. This is somewhat similar to ATC, but instead the operator selects a constant pressure for support instead of the ventilator automatically calculating the pressure based upon flow volume. Therefore, when selecting PSV, the user can use the real-time trachea pressure ($P_{TRACHEA}$) as direct feedback to determine the appropriate pressure assist level. For example, while observing the real-time trachea pressure waveform, the user can adjust the pressure support level setting on the ventilator to obtain a trachea pressure that is above, at, or below a desired baseline pressure, depending on the amount of work the caregiver determines is appropriate as the patient progresses through the ventilator weaning process. Alternatively, the user may set the desired trachea pressure (above, at, or below a desired baseline pressure), and the ventilator controller, which is provided access to the $P_{TRACHEA}$ data from the acoustic reflectometry system, may automatically adjust the pressure support level setting on the ventilator to obtain the desired trachea pressure.

Assessing a Patient's Readiness for Weaning

In the prior art, the determination of a patient's readiness for weaning off of a ventilator is assessed by a number of methods, one of which consists of reducing ventilator support to the level that it only overcomes the WOB intrinsic to the artificial airway. If, for an extended period of time prior to extubation, the patient is able to sustain the effort necessary for full spontaneous breathing while the ventilator support level is only overcoming the WOB caused by the artificial airway, extubation is indicated.

Use of measurements from the acoustic reflectometry system in conjunction with the support modes available in ventilators, can significantly increase the validity of the "extubation simulation" (or "electronic extubation") to more accurately reflect a patient's long-term ability to breathe without the help from a ventilator, and make this type of weaning trial a more integral part of the natural progression of a treatment protocol. During electronic extubation, the pressure at the top of the ETT is set so that the pressure at the bottom of the ETT is the pressure that the patient would experience if they were breathing on their own (i.e., the ventilation is compensating only for the effect of the ETT, hence the ETT is said to have been electronically extubated). One embodiment, two sets of WOB parameters are displayed on the ventilator, one that depicts the actual WOB share of the patient versus the ventilator, and one that gives the same parameters under "free airway" conditions as calculated from the continuous information of tube resistance ($R_{TUBE}$) that is available from the acoustic reflectometry system.

Ability to Suggest Cause of High Pressure Alarm

During a high pressure alarm issued by the ventilator, it is possible to provide more specific alarm language to the user based upon information that can be supplied to the ventilator controller from the acoustic reflectometry system. The data received from the acoustic reflectometry system can then be used to diagnose the cause of the high pressure condition, giving the user insight into how to correct the problem that is causing the alarm. Examples of high pressure alarm information that can be transmitted to the user based upon information made available by the acoustic reflectometry system include:

1. Partial obstruction detected in Err;
2. ETT tip partially occluded; and
3. Possible mainstem bronchial intubation (indicated by the size of the passageway detected around the ETT tip).

Ability to Suggest Cause of Low Volume Alarm

During a low volume alarm issued by the ventilator, it is possible to provide more specific alarm language to the user based upon information that can be supplied to the ventilator controller from the acoustic reflectometry system. The data received from the acoustic reflectometry system can then be used to diagnose the cause of the low volume condition, giving the user insight into how to correct the problem that is causing the alarm. Examples of low volume alarm information that can be transmitted to the user based upon information made available by the acoustic reflectometry system include:

1. Possible mainstem bronchial intubation (indicated by the size of the passageway detected distal of the ETT tip);
2. Possible collapsed lung (indicated by a significant change in the airway sonic reflection morphology, which is a composite of the reflection coming from both the left and right lungs—change one lung volume and the composite signal will change significantly);
3. Possible bronchial plug (indicated by a significant change in the airway sonic reflection morphology, which is a composite of the reflection coming from both the left and right lungs—a plugged bronchus of one lung will significantly change the composite signal).

Integration of Acoustic Reflectometry System Data into Hierarchy of Ventilator Alarms Ventilator alarms are calling for intervention when a physical condition been recognized that directly threatens the well-being of a patient. However, in the way alarms and their hierarchies are implemented in ventilators in the prior art, they are also used to improve treatment efficacy by directing the clinician to the most likely source causing the alarm. Using data available from the acoustic reflectometry system, an airway resistance threshold alarm may be created that will be activated before any high pressure alarms would be triggered, effectively giving the clinician an opportunity to solve the problem before a high pressure condition occurs.

Integration of Acoustic Reflectometer into Ventilator/Hose

An acoustic reflectometer as referenced herein may be integrated into the ventilator at the hose connection or in the hose itself. This acoustic reflectometer may be used to detect hose faults and other conditions:

1. Location and severity of hose kinking;
2. Location and severity of hose occlusion due to rainout (the pooling of condensation in a low point of the hose);
3. Hose partial or full disconnection location; or
4. Detect presence/absence of airway circuit devices (filters, etc).

It will be appreciated in view of the present disclosure that the acoustic reflectometer that is integrated into the ventilator at the hose connection or in the hose itself may be in addition to, or as a replacement for, the acoustic reflectometer located near the proximal end of the ETT.

Providing Insights into Ventilator Trending Parameters

Ventilators report trends of different parameters such as peak inspiratory pressure (PIP), airway compliance, respiratory rate (RR), etc. When these values change over time, it is not always clear if the change is related to the patient's condition, factors associated with the artificial airway, or both.

Providing the ability to view ventilation trended variables in concert with the information from the acoustic reflectometry system (including the real-time $R_{TUBE}$ and $P_{TRACHEA}$ calculated as described hereinabove) provides the clinician with a new means to observe correlations between artificial airway issues and changing trending parameters. This information can help the clinician to better understand some of the subtle changes present with auto modes and compensation modes as they relate to changes in patient and artificial airway status.

One example of providing insights into ventilator trending parameters is using trended information from the acoustic reflectometry system to understand why peak pressure has increased over time during volume ventilation. Increased peak pressure can be caused by a number of very different conditions, each of which results in a different response by the clinician. If the increase is due to an increased ETT resistance, then the response would be to remove the constriction from the ETT. If the increase is due to endobronchial intubation, then the response would be to reposition the ETT tip above the carina. If the increase is due to a mechanical change in the patient airways (such as bronchoconstriction) then the response would be to administer a bronchodilator. All of these conditions can be inferred from trends of $R_{TUBE}$, $P_{TRACHEA}$, ETT tip position, and passageway size around ETT tip, in conjunction with the peak pressure. If the increased peak pressure is accompanied by an increased $R_{TUBE}$ or a lack of increased $P_{TRACHEA}$ then it could be inferred that an increased ETT resistance (e.g. mucus obstruction, tube kinking, or patient biting) and not mechanical changes in the patient airways may be contributing to the increased peak pressure. Alternatively, if the increased peak pressure is accompanied by both an ETT tip position that is very low in the trachea and a decreased passageway size around the ETT tip, then it could be inferred that endobronchial intubation and not mechanical changes in the patient airways may be contributing to the increased peak pressure. If the increased peak pressure does not correlate to any of the trended information available from the acoustic reflectometry system, then it could be inferred that mechanical changes in the patient airways may be contributing to the increased peak pressures.

Another example of providing insights into ventilator trending parameters is using trended information from the acoustic reflectometry system to understand why tidal volume has decreased over time during pressure ventilation. As with increased peak pressures during volume ventilation, decreased tidal volume can be caused by a number of very different conditions, each of which results in a different response by the clinician. If the decrease is due to an increased ETT resistance, then the response would be to remove the constriction from the ETT. If the decrease is due to endobronchial intubation, then the response would be to reposition the ETT tip above the carina. If the decrease is due to a mechanical change in the patient airways (such as bronchoconstriction) then the response would be to administer a bronchodilator. As was discussed above, all of these conditions can be inferred from trends of $R_{TUBE}$, $P_{TRACHEA}$, ETT tip position, and passageway size around ETT tip, in conjunction with the tidal volume.

Secretion Management

A recommendation for suctioning the ETT can be generated based upon the value, and optionally the trend, of the artificial airway resistance as measured by the acoustic reflectometry system.

Furthermore, ventilators typically have a specific "mode" that can be invoked for suctioning (e.g., for performing pre-oxygenation, post-oxygenation, etc). Pre-suctioning and post-suctioning measurements for tube resistance may be analyzed and used as a basis for a message that indicates that the suctioning effort was successful or not completely successful. This, in turn, could alert the caregiver to dried secretions that are not removed by regular suctioning and might be an indication for ETT replacement, increased humidification, or other interventions such as use of a "tube rescue" device which removes mucus debris from walls of the ETT lumen. Examples of tube rescue devices include CAM Rescue Cath (available from Omneotech, 92300 Overseas Highway, Suite 208, Tavernier, Fla. 33070) and endOclear (available from Endoclear, LLC, 2390 Mitchell Park Drive B, Petoskey, Mich. 49770).

Cough Detection to Reduce Nuisance Alarms

Patient coughs are significant as they relate to both high pressure alarms and secretion management. The microphones in the acoustic reflectometry system can be used to detect a patient cough event, and this information can be supplied to the ventilator to discriminate for those events. For example, this can be embodied as a "count but ignore cough events" option in the ventilator alarm settings, with the benefit of reducing nuisance alarms.

Cough Detection for Secretion Management

When a cough is detected by the acoustic reflectometry system, a comparison may be made of the ETT condition before and after each cough event in order to assess the effectiveness of the cough as a means for moving secretions (based on the migration of the location of measured Ell obstructions before and after the cough).

Integration of the Acoustic Reflectometry System Into Other Airway Devices

Integration of acoustic reflectometry system information into a medical device is not limited to only ventilators. For example, heated humidifiers can benefit from acoustic reflectometry system information. Issues involving humidifiers are mostly related to rainout, insufficient humidification leading to dried secretions, and general hygiene. The acoustic reflectometry system information relating to the size and location of obstructions offers manufacturers of humidifiers a means to detect specific humidifier-related issues and either direct the clinician to the problem or automatically make device setting adjustments to attempt to address the problem.

Although the teachings of the present disclosure have been described in detail with reference to certain embodiments, variations and modifications exist within the scope and spirit of these teaching as described and defined in the following claims:

What is claimed is:

1. A system for use of acoustic reflectometry in ventilation devices, the system comprising:
   a sound generator to emit sound waves into an endotracheal tube ("ETT");
   at least one sound receiver to detect returning acoustic reflections;
   at least one processor and memory coupled to the sound generator and at the least one sound receiver, the memory including instructions to cause the at least one processer to:
   analyze timings and amplitudes of the returning acoustic reflections to determine a location and size of an ETT obstructions;
   calculate, based on the location and size of an ETT obstruction, flow resistance within the ETT; and
   estimate a pressure drop across the ETT using the calculated flow resistance when a patient spontaneously breathes.

2. The system of claim 1, further comprising a pressure sensor and a flow sensor in an airway circuit.

3. The system of claim 1, further comprising a pressure sensor and a flow sensor in an airway circuit, wherein the memory includes instructions to cause the at least one processor to determine a pressure within the trachea of the patient based on an algorithm that implements an equation generally of the form:

$$P_{TRACHEA} = P_{AW} - R_{TUBE} \times \text{Flow},$$

where $P_{TRACHEA}$=tracheal pressure, $P_{AW}$=mean pressure at a Y-piece, $R_{TUBE}$=flow resistance parameter, Flow=airway flow.

4. The system of claim 3, wherein the memory includes instructions to cause the at least one processor receive manual input from a user to obtain a trachea pressure that is above, at, or below a desired baseline pressure, when the user is monitoring real-time tracheal pressure calculated using the algorithm.

5. The system of claim 3, wherein the system is configured to display a first set of work of breathing ("WOB") parameters based on an actual WOB share of the patient versus a ventilation device and a second set of WOB parameters based on the algorithm, wherein a comparison of the first set of parameters with the second set of parameters is indicative of a patient's readiness for weaning off the ventilation device.

6. The system of claim 2, wherein instructions further cause the at least one processor to issue an alarm when a predetermined high pressure is detected and, wherein the system is further configured to determine a possible cause of the high pressure alarm and to display information that there is a partial obstruction detected in the ETT, the ETT tip is partially occluded, a possible mainstem bronchial intubation, or any combination thereof.

7. The system of claim 2, instructions further cause the at least one processor to:
   issue an alarm when a predetermined low volume is detected;
   determine a possible cause of the low volume alarm; and
   display information that there is a possible mainstem bronchial intubation, a possible collapsed lung, a possible bronchial plug, or any combination thereof.

8. The system of claim 1, wherein instructions further cause the at least one processor to issue an alarm using a hierarchy that is determined by acoustic reflection information.

9. The system of claim 3, wherein the instructions further cause the at least one processor to simultaneously display ventilation trended variables along with trended tracheal pressure calculated by the algorithm, trended ETT resistance calculated by the algorithm, trended ETT obstruction percentage, trended passageway size around the ETT tip, trended relative movement of the ETT tip within a trachea, or any combination thereof to assist the user in diagnosing changes in the ventilation trended variables.

10. The system of claim 3, wherein instructions further cause the at least one processor to indicate when to suction the ETT based on a trend of the flow resistance parameter calculated using the algorithm.

11. A system for use of acoustic reflectometry in ventilation devices, the system comprising:
   a sound generator to emit sound waves into an endotracheal tube "ETT");
   at least one sound receiver to detect returning acoustic reflections;
   a reflectometry device having a controller for analyzing timings and amplitudes of the returning acoustic reflections to determine reflectometry data including a size of a passageway around an ETT tip, location and size of ETT obstructions, relative movement of the ETT tip within a trachea, or any combination thereof; and
   a ventilation device having a pressure sensor and a flow sensor in an airway circuit and being configured to:
      analyze data from the pressure sensor and the flow sensor;
      based on the analysis of the data from the pressure sensor and the flow sensor, issue an alarm when a predetermined high pressure is detected; and
      in response to issuing the alarm, determine, based on the reflectometry data, a possible cause of the high pressure and display information that there is a partial obstruction detected in the ETT, the ETT tip is partially occluded, a mainstem bronchial intubation, or any combination thereof.

12. The system of claim 11, wherein displaying information includes displaying a trend of ETT tip position over time.

13. The system of claim 11, wherein displaying information includes displaying a trend of ETT resistance over time.

14. A system for use of acoustic reflectometry in ventilation devices, the system comprising:
   a sound generator to emit sound waves into an endotracheal tube ("ETT");
   at least one sound receiver to detect returning acoustic reflections;
   a reflectometry device having a controller for analyzing timings and amplitudes of the returning acoustic reflections to determine reflectometry data including a size of a passageway around an ETT tip, location and size of ETT obstructions relative movement of the ETT tip \vithin a trachea, or any combination thereof; and
   a ventilation device having a pressure sensor and a flow sensor in an airway circuit and being configured to:
      analyze data from the pressure sensor and the flow sensor;
      based on analyzing the data from the pressure sensor and the flow sensor, issue an alarm when a predetermined low volume flow is detected;
      in response to the alarm, determine, based on the reflectometry data, a possible cause of the low volume flow; and
      display information that there is a possible mainstem bronchial intubation, a possible collapsed lung, a possible bronchial plug, or any combination thereof.

15. The system of claim 14, wherein displaying information includes displaying a change in airway sonic reflection morphology.

16. The system of claim 14, wherein displaying information includes displaying a change in a size of the passageway detected distal of the ETT tip over time.

17. A system for use of acoustic reflectometry in ventilation devices, the system comprising:
   a sound generator to emit sound waves into an endotracheal tube ("ETT");
   at least one sound receiver to detect returning acoustic reflections;
   a reflectometry device having a controller for analyzing timings and amplitudes of the returning acoustic reflections to determine reflectometry data including a size of a passageway around an ETT tip, location and size of ETT obstructions, relative movement of the ETT tip within a trachea, or any combination thereof; and
   a ventilation device having at least one processor and memory and including a second sound generator, a second sound receiver, or any combination thereof, within a ventilator hose or the ventilation device, the ventilation device configured to detect, based on at least one measurement of the second sound receiver, faults in a hose connected between the ventilation device and the ETT, the faults including at least one of the location and severity of hose kinking, the location and severity of hose occlusion due to pooling of condensation in the hose, hose partial or full disconnection location from the ETT or the ventilation device, or the presence or absence of airway circuit devices.

18. The system of claim 17, wherein the reflectometry device is configured to display information including the location and severity of the hose occlusion.

19. The system of claim 17, wherein the reflectometry device is configured to display information including the hose partial or full disconnection location.

20. The system of claim 17, wherein the reflectometry device is configured to display information including the location and severity of the hose kinking.

* * * * *